United States Patent
Winterton et al.

(10) Patent No.: US 6,729,326 B1
(45) Date of Patent: May 4, 2004

(54) NEONATAL VALVED MANIFOLD

(75) Inventors: Reed F. Winterton, Salt Lake City, UT (US); Thomas E. McGee, Salt Lake City, UT (US); J. Dale Poplin, Draper, UT (US)

(73) Assignee: Sorenson Medical, Inc., West Jordan, UT (US)

( * ) Notice: Subject to any disclaimer, the term of this patent is extended or adjusted under 35 U.S.C. 154(b) by 386 days.

(21) Appl. No.: 09/723,011

(22) Filed: Nov. 27, 2000

(51) Int. Cl.[7] .............................................. A61M 15/00
(52) U.S. Cl. ............................... 128/203.12; 128/207.16
(58) Field of Search ........................ 128/200.24, 200.26, 128/202.27, 203.12, 205.24, 207.14, 207.12, 207.15–207.16, 909, 912; 604/30, 33, 35, 246–250, 290, 905, 171; 251/280, 142, 149, 208, 205, 206, 209, 217, 320, 322; 137/907, 908

(56) References Cited

U.S. PATENT DOCUMENTS

| | | | | |
|---|---|---|---|---|
| 4,193,406 A | * | 3/1980 | Jinotti | 128/204.18 |
| 4,705,073 A | * | 11/1987 | Beck | 137/625.25 |
| 4,967,743 A | * | 11/1990 | Lambert | 128/202.16 |
| 5,088,486 A | * | 2/1992 | Jinotti | 128/207.14 |
| 5,140,983 A | | 8/1992 | Jinotti | |
| 5,309,902 A | * | 5/1994 | Kee et al. | 128/202.27 |
| 5,333,606 A | * | 8/1994 | Schneider et al. | 128/200.24 |
| 5,333,607 A | | 8/1994 | Kee et al. | |
| 5,354,267 A | | 10/1994 | Niermann et al. | |
| 5,357,946 A | | 10/1994 | Kee et al. | |
| 5,433,195 A | * | 7/1995 | Kee et al. | 128/207.14 |
| 5,445,141 A | | 8/1995 | Kee et al. | |
| 5,487,381 A | | 1/1996 | Jinotti | |
| 5,598,840 A | * | 2/1997 | Iund et al. | 128/207.14 |
| 5,642,726 A | | 7/1997 | Owens et al. | |
| 5,730,123 A | | 3/1998 | Lorenzen et al. | |
| 5,735,271 A | * | 4/1998 | Lorenzen et al. | 128/207.16 |
| 5,746,199 A | * | 5/1998 | Bayron et al. | 128/205.24 |
| 5,882,348 A | * | 3/1999 | Winterton et al. | 604/537 |
| 5,919,174 A | * | 7/1999 | Hanson | 604/533 |
| 6,427,691 B1 | * | 8/2002 | Jinotti | 128/205.24 |
| 6,516,800 B1 | * | 2/2003 | Bowden | 128/204.18 |
| 6,516,803 B1 | * | 2/2003 | Enzinger | 128/207.16 |

* cited by examiner

Primary Examiner—Aaron J. Lewis
Assistant Examiner—Teena Mitchell
(74) Attorney, Agent, or Firm—TraskBritt (57) ABSTRACT

A manifold assembly useful in patient ventilation/aspiration systems includes a stop cock valve with a hollow stem and a transverse slot arranged to permit the stem to be rotated between open and closed positions. In both positions, a ventilating pathway is maintained through the slot and the stem between ventilator and patient connection ports of the manifold. In open position the stem provides a travel pathway for a catheter between the patient connection port and an access port of the manifold. In closed condition, the stem seals this travel pathway. Catheter depth finding features and internally walled manifold structure for direction of respiratory therapy fluids particularly useful for neonatal patients are presented.

20 Claims, 6 Drawing Sheets

NEONATAL VALVED MANIFOLD

BACKGROUND OF THE INVENTION

1. Field

This invention relates generally to valved manifold devices, and is specifically directed to such devices in medical conduit systems. It provides a valved manifold particularly useful at the patient intubation interface of endotracheal ventilation/aspiration systems.

2. State of the Art

Many gas delivery systems, particularly in a hospital or laboratory environment, utilize manifold devices for directing fluid flow. There is a variety of circumstances in which it is necessary or desirable to provide multiple, yet isolated, other path ways through the interior of such a manifold. The manifold is often associated with other components as a system. When the individual components of such a system are subjected to mechanical forces tending to rotate one component with respect to another, it is often essential to provide that travel path through a joint structure which permits rotating or swiveling movement.

As an example, closed systems for endotracheal suctioning and ventilating typically include a manifold enabling introduction of ventilating gases and intermittent exhalation of patient breath simultaneously with insertion and operation of a tracheal suctioning catheter. The manifold structure typically includes multiple ports, usually the open ends of respective conduits extending from a common chamber. One such port is interfaced to a patient through a patient connection device. The suction catheter is often included within an assembly which is connectable to a second port of the manifold. The catheter assembly conventionally includes a collapsible plastic envelope positioned to entirely surround the catheter. A practitioner manually externally collapses the envelope onto the external surface of the catheter, and advances the catheter through the manifold into an access tube connected to a patient, retracting the catheter in a similar fashion following the aspiration procedure.

The manifold thus provides a first pathway for ventilation gases, and a second pathway for the catheter. The catheter provides isolation from the ventilating gases for fluids withdrawn from the patient through the manifold. When the catheter is withdrawn, it is often desired to continue regulated ventilation through the manifold. In some cases, it is desirable for the catheter assembly to be disconnected from the manifold, without disturbing the ventilation of the patient. It is thus necessary to provide for a gas tight sealing of the pathway formerly occupied by the catheter upon its removal. Previous efforts in this connection have involved the provision of auxiliary sealing structures for use in association with the manifold. These arrangements have had several disadvantages. Because they have not been integral with the manifold, their use has been inconvenient in practice. With ventilation ports substantially transverse patient interface ports, air turbulence has been disruptive to potentially delicate and fragile ventilation flow. Certain resilient seals have been unacceptable because they lack the positive sealing characteristics of a mechanical valve. Available valves are not suitable for incorporation into a manifold because they lack the essential capability of providing a travel path for a catheter when catheter suction is needed. Any sealing arrangement employed should be as inexpensive as possible, thereby eliminating complex mechanical valve assemblies from practical consideration.

Material prior art structures and methods are described, among other places, in U.S. Pat. No. 5,333,607 to Kee, et al.; U.S. Pat. No. 5,354,267 to Niermann, et. al.; U.S. Pat. Nos. 5,357,946 and 5,445,141 to Kee, et. al.; U.S. Pat. Nos. 5,140,983 and 5,487,381 to Jinotti; U.S. Pat. No. 5,882,348 to Winterton et al.; U.S. Pat. Nos. 5,735,271 and 5,730,123 to Lorenzen et al. and U.S. Pat. No. 5,642,726 to Owens et al. These patents each disclose ventilator manifold devices and systems in which those devices are utilized. The '267 patent, for example, discloses a manifold and a multi-position stop cock valve. The valve is provided with a "Tee" shaped internal stem channel pattern so that the stem may be positioned selectively to wash the internal lumen of a catheter, to irrigate the patient or to accommodate travel of the catheter through the stem to suction the patient. The valve may be plugged directly into an access port of the manifold. Patient ventilation is conducted without respect to the valve through other ports of the manifold. The valve itself constitutes an integral component of a catheter assembly, and must be removed from the manifold with the remainder of that assembly. The '348 patent discloses a valved manifold embodying a multi-position stop cock valve. The ventilation port is transverse the patient interface port, and is thus characterized by more dead air space than is generally regarded as acceptable for neonatal applications.

A neonatal closed system suction catheter assembly of Alcove Medical, Inc. of Salt Lake City, Utah, Bird Products Corporation of Palm Springs, Calif., and Corpak, Inc. of Wheeling, Ill. includes a depth-finding feature comprising a ring snugly but slidingly surrounding a suction catheter within a collapsible plastic envelope that carries the catheter. After the catheter is advanced to the desired depth, the ring is moved to a point immediately adjacent the manifold. This feature enables a respiratory care practitioner to establish a limit upon the depth to which a suction catheter is insertable into a patient. Accordingly, optimal placement of the catheter tip, once established, need not be reestablished when the catheter is withdrawn and subsequently reinserted. In practice, however, manipulation of the ring from outside the envelope is insufficiently facile.

There remains a need for an inexpensive, yet reliable, manifold assembly incorporating a valve positioned to minimize dead air space within the manifold and capable of passing a catheter. The valve must provide a sealed gas flow path through the manifold in both its open and closed conditions with respect to catheter travel. The manifold should further be removable from any associated catheter assembly. Ideally, the manifold should also include a ventilation port that is substantially axially aligned with the patient interface port. Particularly in neonatal applications, there remains a need for a manifold constructed to minimize fluid flow turbulence of ventilating gases and to minimize the likelihood of respiratory therapy fluids introduced through an aspiration portion of a device from back-washing into a ventilation portion of the device.

A further need remains for a patient ventilation/aspiration system wherein the desired depth of successive insertions of the suction catheter can be established by a single initial procedure by means that are external to the collapsible plastic envelope.

SUMMARY OF THE INVENTION

The invention may be embodied as a multi-function manifold positioned at the distal end of a catheter assembly. A catheter tube is slidable lengthwise through a passageway, which includes a first (distal) port at the distal side of the manifold and a second (proximal) port near the proximal side of the manifold. The distal and proximal ports are generally not in alignment. Accordingly, the catheter should be sufficiently flexible to accommodate a bend as it travels through the passageway. A special valve is positioned along the passageway in axial alignment with the distal side, thereby to minimize dead air space and ventilation turbulence. This valve may be operated to open a travel path for the catheter through the manifold. The manifold preferably includes a patient connection conduit at its distal side for attachment to (and communication with) an indwelling intubation device, such as a tracheal tube, endotracheal tube or nasopharyngeal tube. The manifold also includes a ventilating structure extending transversely from (and in fluid communication with) the distal end and the passageway. The ventilating structure constitutes means for selectively introducing ambient air, oxygenated air and other therapeutic gasses into the respiratory system of the patient. Other conduits may also be provided for the introduction of therapeutic and diagnostic implements and for the introduction of other suitable gases and lavage, surfactant and oxygenation solutions to the respiratory system.

The manifold, and in particular, the manifold valve, is structured and arranged to enable simultaneous patient ventilation and protected tracheal suctioning. A suctioning catheter may be coupled at its proximal end to a suctioning valve. The distal end of the catheter may then be fed through a conduit near the proximal side of the manifold for reciprocal movement through the intubation device. The catheter is often provided in an assembly, whereby it is enveloped by a protective barrier that enhances and preserves cleanliness, which is coupled to an access structure near the proximal side of the manifold. The manifold and valve may be integral with the catheter assembly, but are preferably detachable to facilitate multiple uses of the manifold, either in association with other assemblies or for other applications.

The manifold valve is structured and arranged as a stopcock with a specialized valve stem. The valve stem is fashioned to provide the previously described versatility of function to the manifold. The manifold may thus be positioned in a patient ventilating circuit in conventional fashion to function as a portion of that circuit. In that circumstance, the valve stem is positioned to maintain a first, ventilating, flow path through the manifold, including through a portion of the stem. As so positioned, the stem blocks flow through other selected travel paths within the manifold. In particular, the passageway required for the catheter, when it is present, is sealed against gas flow by the stem. The stem may be repositioned to permit passage of a catheter through a slot in the stem, while still maintaining the ventilation flow path in open condition.

A preferred valved manifold assembly includes a stopcock valve with a hollow stem and a transverse slot arranged to permit the stem to be rotated between open and closed positions. In both positions, a substantially axially-aligned ventilating fluid flow pathway is maintained through the stem between ventilator and patient connection ports of the manifold. In open position, the stem provides a travel pathway for a catheter between the patient connection port and an access port of the manifold. In closed condition, the stem seals this travel pathway. This structure is ideally suited for inclusion in patient ventilation/aspiration systems which would benefit from less dead air space and less turbulence in the flow of ventilation gas.

In summary, an interface assembly for closed system endotracheal ventilating and aspirating procedures may be embodied as a manifold having a proximal manifold end and a distal manifold end. The manifold includes a ventilating port at its proximal end, in open communication with an interior chamber; a patient connection port at its distal end, also in open communication with the interior chamber and further in substantial registration with the ventilation port; and an access port which may be at the proximal end and which is in communication with the interior chamber and substantially out of registration with the patient connection port. Accordingly, a fluid flow path is formed through the interior chamber between the ventilation port and the patient connection port. The access port and patient connection ports are positioned to provide a catheter travel pathway through the access port, the interior chamber and the patient connection port. The catheter travel pathway and fluid flow path in a typical embodiment may be separated throughout the interior chamber between the proximal manifold end and the distal manifold end by a wall. In such an embodiment, an irrigation access tube may be provided in fluid communication with the access port, whereby respiratory therapy fluid may be introduced. This arrangement advantageously enables the introduction of surfactants, oxygenation liquids, saline lavage and other fluids for respiratory therapy without exposing the ventilation circuit and the fluid flow path to such therapeutic fluids.

The assembly further includes a valve comprising a valve stem positioned within the catheter travel pathway. The stem is constructed and arranged for movement between first and second positions. In the first position, the stem blocks the pathway. In the second position, the stem provides a portion of the catheter travel pathway. Actuation structure may be associated with or linked to the stem and manually operable to move the stem between the first and second positions. The valve is further constructed and arranged to avoid blocking gas flow between the ventilation port and the patient connection port.

In a typical embodiment, the access port is oriented generally transverse the patient connection port while the ventilation port is generally axially aligned with the patient connection port. The valve stem is ideally positioned within the interior chamber and is structured with a hollow center cavity opening towards the ventilation port. The hollow center is in open communication with the patient connection port, typically by means of a slot transverse the cavity and in registration with the patient connection port when the stem is in either the first or second positions. The stem includes a wall with an outer surface in sealing relationship with the access port when the stem is in the first position. An opening through the wall into the cavity is positioned and configured to register with the access port when the stem is in the second position.

In use, the manifold assembly is interposed between an indwelling tube at the distal end of the manifold and a ventilating circuit at the proximal end. These junctions may embody a swivel configuration to permit left or right bedside placement of the catheter assembly, and free rotation of the ventilation circuit and patient connection relative to the catheter assembly to reduce the risk of extubation. The apparatus is structured and arranged to permit connection between tubular elements or conduits associated with such components. It is uniquely useful for connecting the manifold of this invention into endotracheal ventilating and aspirating assemblies.

The access port of the interface assembly may be structured and arranged to accommodate axial advancement and retraction of the catheter assembly while maintaining positive end expiratory pressure within the interior chamber. In such an embodiment the catheter assembly may include a suction catheter with a proximal end, a distal end portion for advancement through the access port and a clip associated with the suction catheter. The clip is selectively located at a point that defines the transition from the distal end portion and the proximal end and, thus, the proximal end is prevented from being advanced beyond the access point. In a preferred embodiment, a flexible sheath carries and substantially envelopes the suction catheter, and the clip is positioned outside the flexible sheath and is selectively attachable to the catheter through the sheath to selectively define the transition point between the proximal end and the distal end portion. In use, the ideal depth to which to advance the distal end portion of the catheter for a suctioning procedure need only be determined once. In subsequent procedures, the clip serves as a depth marker.

BRIEF DESCRIPTION OF THE DRAWINGS

In the drawings, which illustrate what is currently regarded as the best mode for carrying out the invention.

DETAILED DESCRIPTION OF THE ILLUSTRATED EMBODIMENT

The figures illustrate embodiments including a stopcock manifold valve (also referred to as an interface assembly) designated generally 22. The valve 22 includes a knob 24, which may be turned by finger pressure to rotate a stem 26. The stem 26 is structured with an open interior (also referred to as an interior chamber) 28, defined by a continuous wall 32. When the stem 26 is installed within the manifold body 34 of the valve, as shown by FIG. 2, the open bottom 6f the open interior 28 registers with a first manifold port 40 (also referred to as a ventilation port 40). The knob 24 may comprise a portion of the first manifold port 40, as illustrated.

Figure 1:
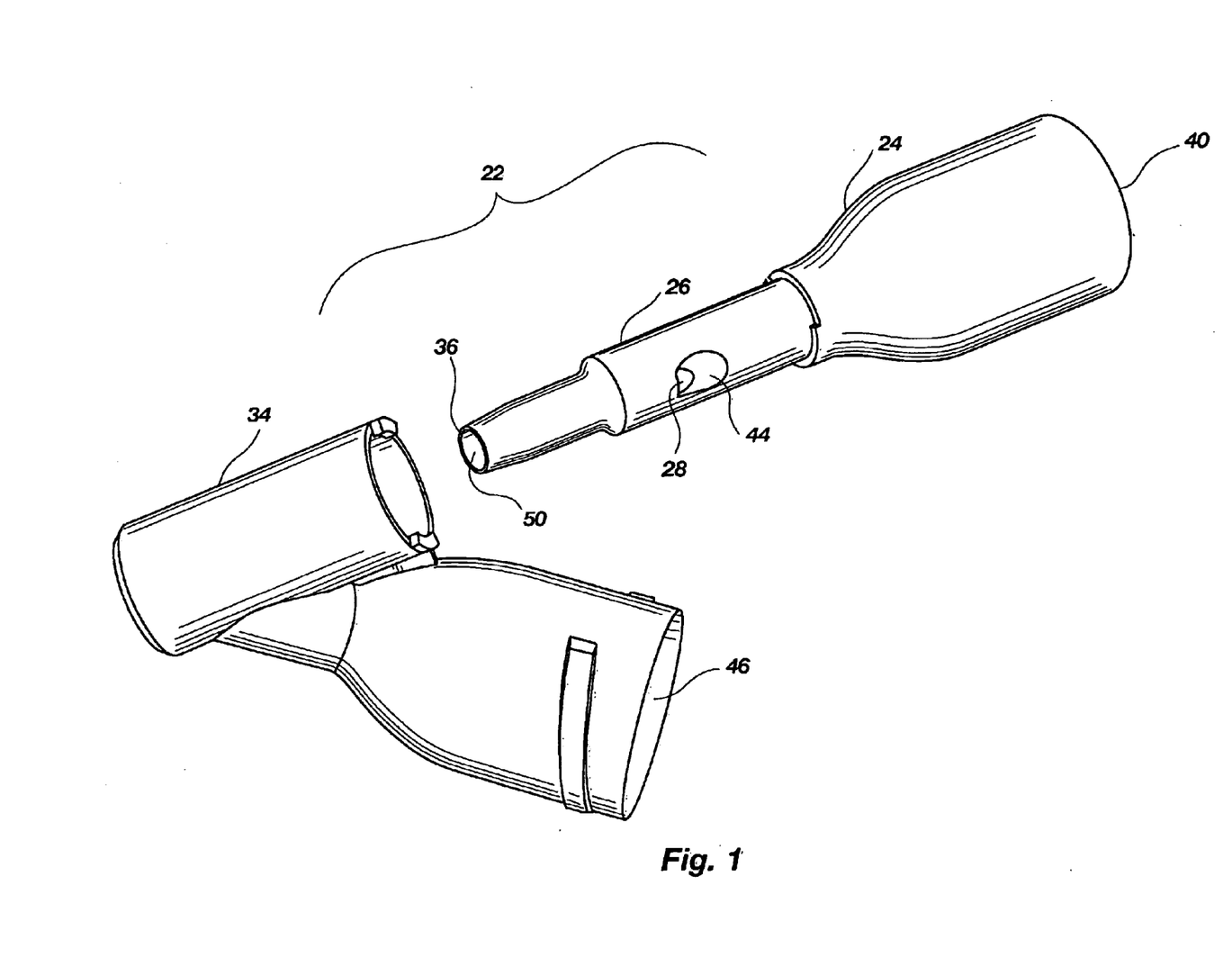
FIG. 1 is an exploded pictorial view of a valved manifold of this invention.
Figure 2:
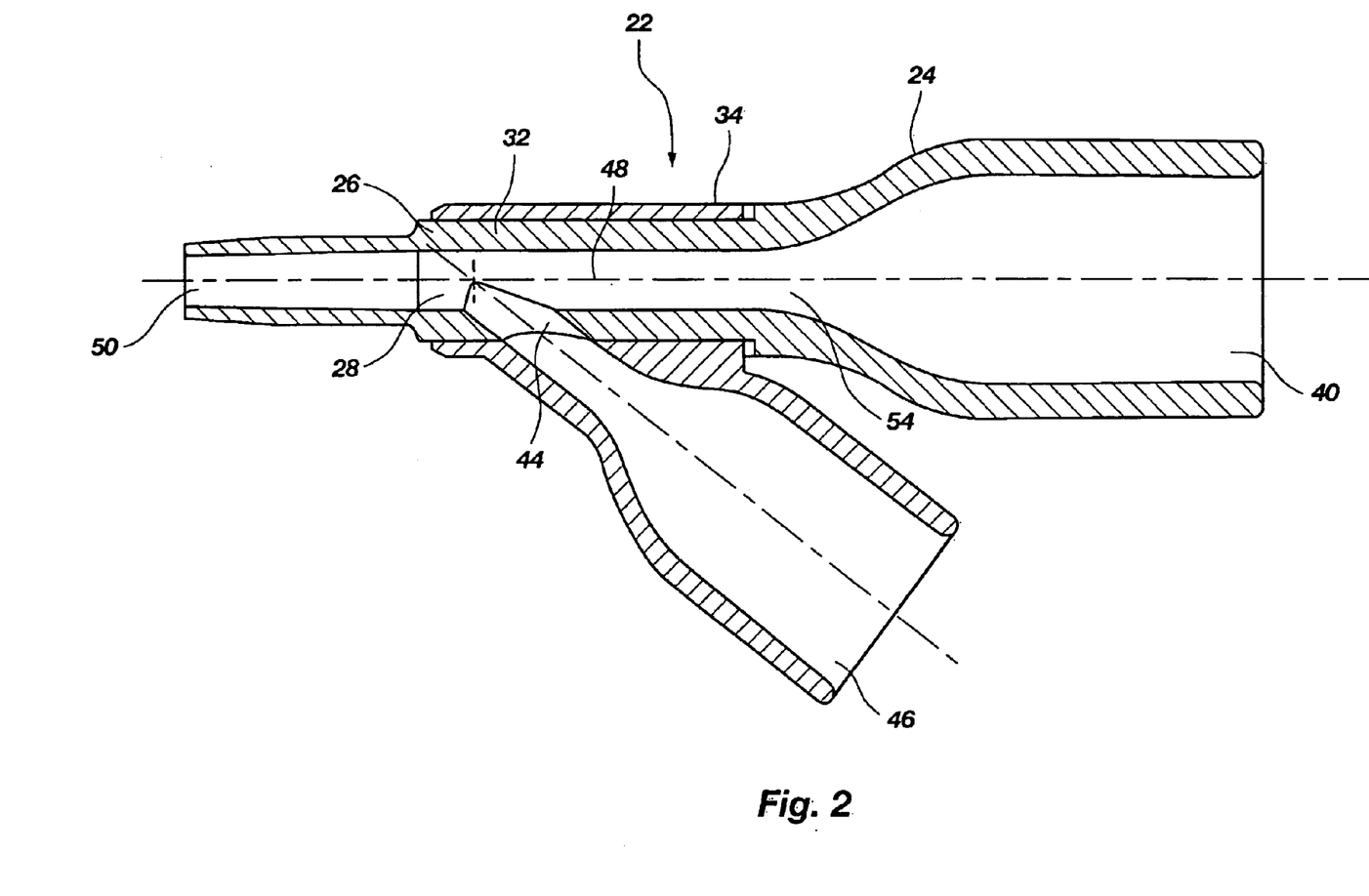
FIG. 2 is a cross sectional view in elevation of the valved manifold of FIG. 1, in assembled condition.

The stem 26 may be rotated between a first, closed position in which a solid portion 48 of the wall 32 is brought into registration with a second manifold port (also referred to as an access port) 46 and a second, open position, as illustrated by FIGS. 1 and 2, wherein an opening 44 of the wall 32 registers with the second manifold port 46. In the second position, a travel path (also referred to as a catheter travel pathway) is opened between the second manifold port 46 and a third manifold port (also referred to as a patient connection port) 50 through the open interior 28 of the stem 26. In the first position, the port 46 is sealed. In both positions of the stem 26, a fluid flow pathway 54 through the continuous wall 32 provides a flow path that is substantially axially aligned between the third port 50 and the first port 40 through the stem interior 28. Thus, in either position, the first manifold port 40 remains in open, fluid flow communication with the third manifold port 50. The knob 24 may alternatively be formed as a portion of the second manifold port 46 (not shown).

Figure 3:
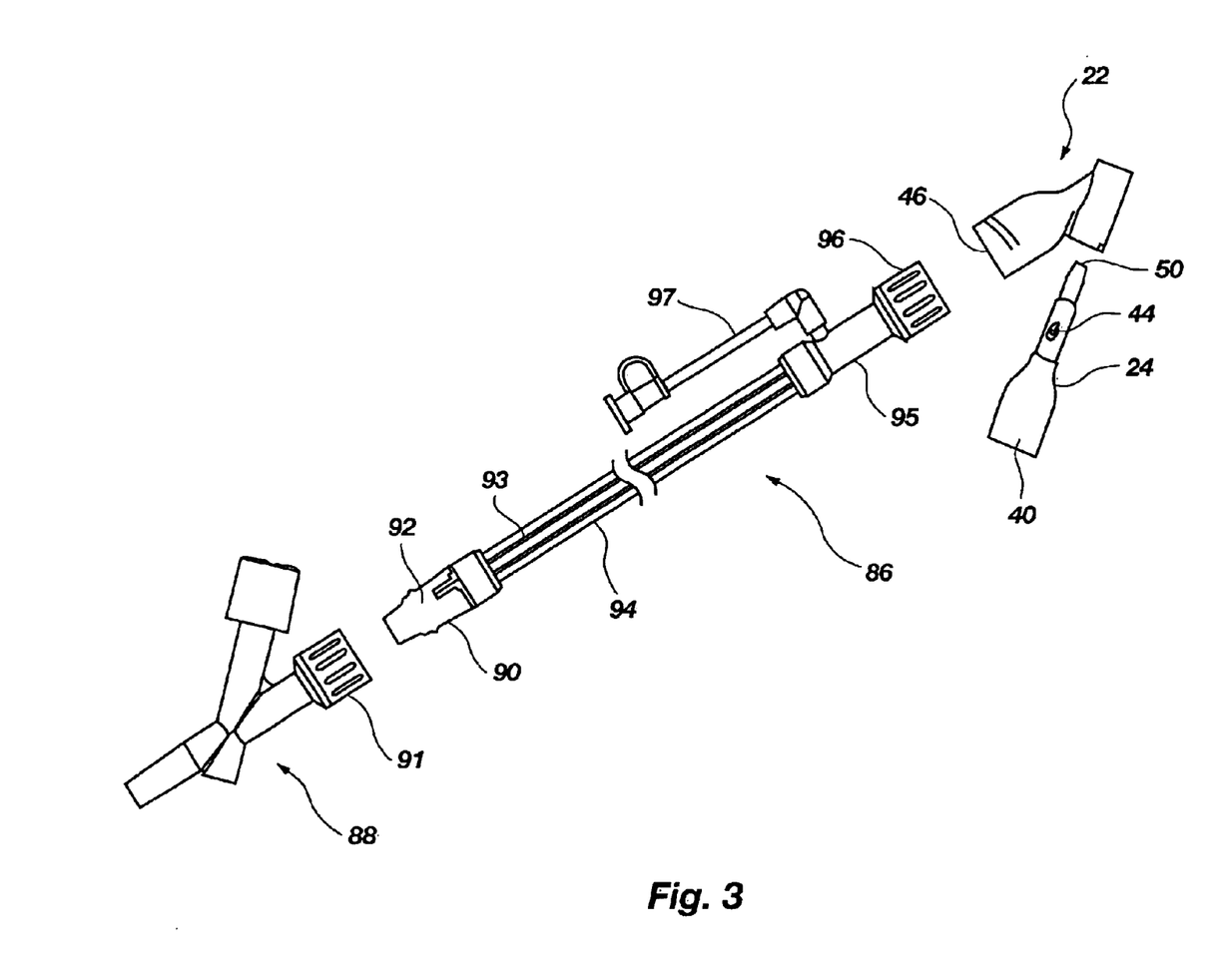
FIG. 3 is an exploded plan view, partially broken away, illustrating the manner in which the valved manifold of FIG. 1 may be connected in operable association with components of a suction catheter assembly.
Figure 4:
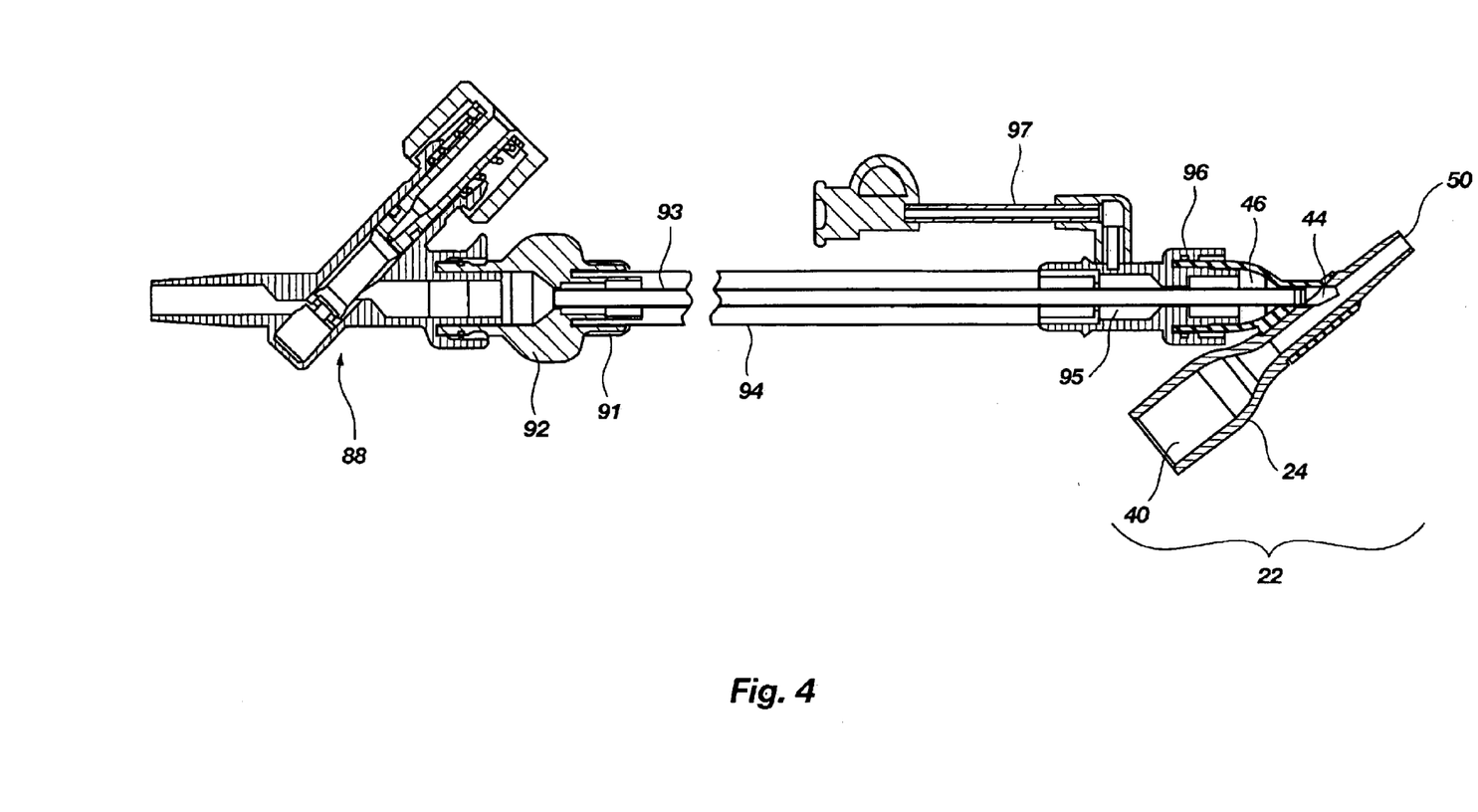
FIG. 4 is a cross sectional view of the assembly shown by FIG. 3.
Figure 5:
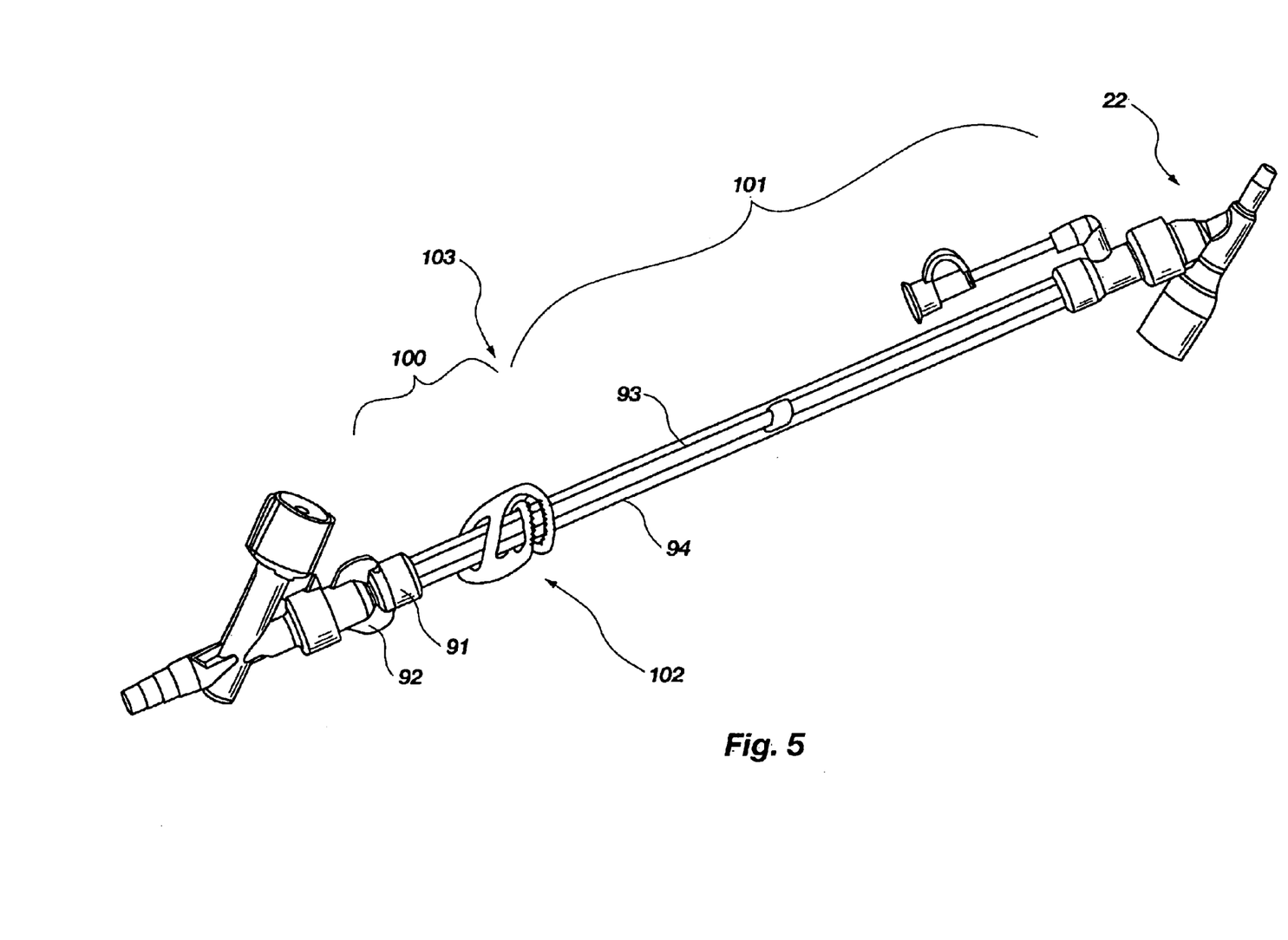
FIG. 5 is a pictorial view of the assembly of FIG. 3, additionally illustrating both prior art and novel catheter depth finding features.

Referring to FIGS. 3 and 4, the manifold valve 22 is shown in association with a catheter assembly, designated generally 86. A suction control valve, generally 88, is connected to the proximal end 90 of the assembly 86 by means of a luer collar 91 and wing connector 92. A suction catheter 93 is carried within, and is substantially enveloped by, a flexible sheath 94. It may thus be selectively extended or withdrawn (by manual manipulation through the sheath) through a sputum trap 95, which is in turn connected by a luer collar 96 to the access port 46 of the manifold 22. An irrigation access tube 97 extends from the sputum trap 95. In its open condition, the catheter 93 may be manipulated through the valve 22 into a patient intubation fixture (not shown). The system is then sealed against leakage of respiration gases passing into the manifold ventilator port by sealing structure within the sputum trap 95. With the catheter 93 withdrawn, the knob 24 may be turned to closed condition. The luer collar 96 may then be turned to release the assembly 86 from its connection to the valved manifold 22. Aspiration/ventilation may then continue through the patient connection 50 and ventilator 40 ports.

The access port 46 of the interface assembly 22 may be structured and arranged to accommodate axial advancement and retraction of the suction catheter 93 while maintaining positive end expiratory pressure within the interior chamber 28. In such an embodiment the suction catheter 93 may include, as set forth in FIG. 5, a proximal end, designated generally 100, a distal end portion, designated generally 101, for advancement through the access port and a clip 102 associated with the suction catheter 93. The clip is selectively located at a transition point 103 that defines the transition from the distal end portion 101 and the proximal end 100. The proximal end is thereby prevented from being advanced beyond the access port 46. In a preferred embodiment, a flexible sheath 94 carries and substantially envelopes the suction catheter 93, and the clip 102 is positioned outside the flexible sheath 94 so that it is selectively attachable to the suction catheter 93 through the flexible sheath 94 to selectively define the transition point 103 between the proximal end 100 and the distal end portion 101. Accordingly, in use, the ideal depth to which to advance the distal end portion 101 of the suction catheter 93 for a suctioning procedure need only be determined once. In subsequent procedures, the clip 102 serves as a depth marker.

Figure 6:
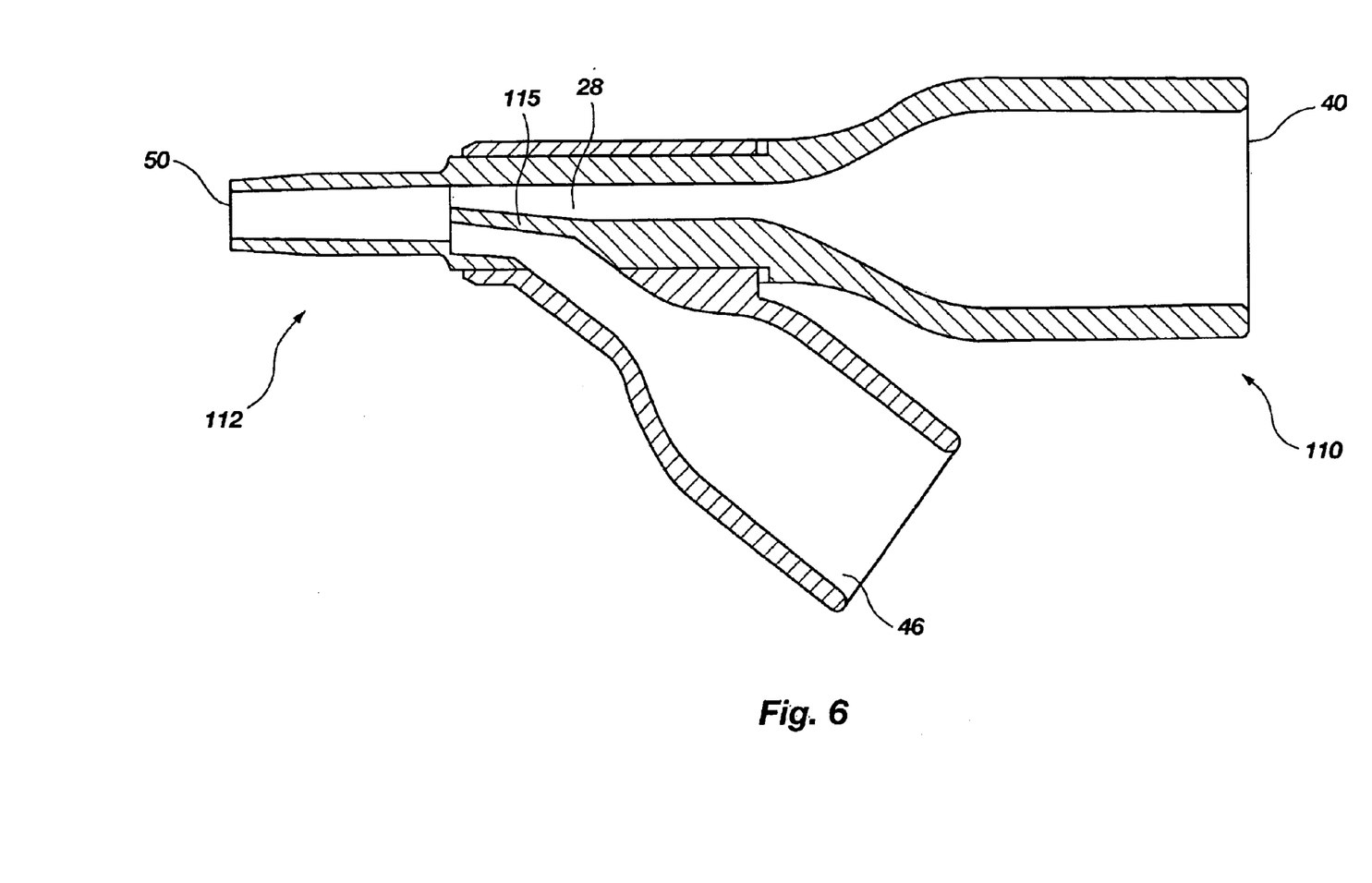
FIG. 6 is a view similar to FIG. 2, illustrating an alternative embodiment of the valved manifold of the invention.

As best illustrated in FIG. 6, the catheter travel pathway and fluid flow pathway 54 in one embodiment may be separated throughout the interior chamber 28 between a proximal manifold end, generally designated 110, and a distal manifold end, generally designated 112, by a wall 115. In such an embodiment, the irrigation access tube 97 is in fluid communication with the access port 46 whereby respiratory therapy fluid may be introduced, advantageously enabling introduction of surfactants, oxygenation liquids, saline lavage and other fluids for respiratory therapy without exposing a ventilation circuit and the fluid flow pathway 54 to such therapeutic fluids.

Reference in this disclosure to details of the illustrated or other preferred is not intended to limit the scope of the appended claims, which themselves recite regarded as important to the invention.

What is claimed is:

1. A valve for use in a patient ventilation/aspiration system, comprising:
   a chamber, including first, second and third ports and a fluid flow path established between the first and third ports, said first and third ports being substantially axially-aligned;

a valve comprising a stem positioned within said chamber, said stem being constructed and arranged for movement between
  a first position in which said stem blocks fluid flow through said second port; and
  a second position in which said stem provides a portion of a catheter travel pathway between said second and third ports, said portion of said catheter travel pathway comprising a portion of the fluid flow path throughout said third port; and
actuation structure linked to said stem and operable to move said stem between said first and second positions;
said valve being further constructed and arranged to avoid blocking fluid flow between said first and third ports.

2. A valve according to claim 1, wherein said stem has a hollow center cavity opening towards said first port, said hollow center cavity being in open communication with said third port.

3. A valve according to claim 2, wherein said stem includes a slot transverse said hollow center cavity, said slot being positioned in registration with said third port when said stem is in either of said first or second positions.

4. A valve according to claim 3, wherein said stem includes:
  a wall with an outer surface in sealing relationship with said second port when said stem is in said first position; and
  an opening through said wall into said hollow center cavity, said opening being positioned and configured to register with said second port when said stem is in said second position.

5. An interface assembly for closed system endotracheal ventilating and aspirating procedures, comprising:
  a manifold having a ventilation port in open communication with an interior chamber;
  a patient connection port in open communication with said interior chamber and forming a fluid flow path with said ventilation port, said patient connection port being substantially in registration with said ventilation port; and
  an access port in communication with said interior chamber and substantially out of registration with said patient connection port;
  said access port and patient connection port being positioned to provide a catheter travel pathway through said access port, said interior chamber and said patient connection port, said catheter travel pathway including that portion of the fluid flow path from said interior chamber throughout said patient connection port; and
  a valve, comprising:
    a stem positioned within said catheter travel pathway, and constructed and arranged for movement between
      a first position in which said stem blocks said catheter travel pathway, and
      a second position in which said stem provides a portion of said catheter travel pathway; and
    actuation structure linked to said stem and operable to move said stem between said first and second positions;
    said valve being further constructed and arranged to avoid blocking fluid flow between said ventilation port and said patient connection port.

6. An assembly according to claim 5, wherein said access port is oriented generally transverse said fluid flow path.

7. An assembly according to claim 6, wherein said stem is positioned within said interior chamber.

8. An assembly according to claim 7, wherein said valve stem has a hollow center cavity opening towards said ventilation port, said hollow center cavity being in open communication with said patient connection port.

9. An assembly according to claim 8, wherein said valve stem includes a slot transverse said hollow center cavity, said slot being positioned in registration with said patient connection port when said stem is in either of said first or second positions.

10. An assembly according to claim 9, wherein said stem includes:
  a wall with an outer surface in sealing relationship with said access port when said stem is in said first position; and
  an opening through said wall into said hollow center cavity, said opening being positioned and configured to register with said access port when said stem is in said second position.

11. An interface assembly for closed system endotracheal ventilating and aspirating procedures, comprising:
  a manifold having:
    a ventilation port in open communication with an interior chamber;
    a patient connection port in open communication with said interior chamber and forming a fluid flow path with said ventilation port, said patient connection port being substantially in registration with said ventilation port; and
    an access port in communication with said interior chamber and substantially out of registration with said patient connection port;
    said access port and patient connection port being positioned to provide a catheter travel pathway through said access port, said interior chamber and said patient connection port, said catheter travel pathway including that portion of the fluid flow path from said interior chamber throughout said patient connection port; and
  a valve, comprising:
    a stem positioned within said interior chamber constructed and arranged for movement between:
      a first position in which said stem blocks fluid flow through said access port; and
      a second position in which said stem provides a portion of said catheter travel pathway; and
    actuation structure linked to said stem and operable to move said stem between said first and second positions;
    said valve being further constructed and arranged to avoid blocking fluid flow between said ventilation port and said patient connection port.

12. An assembly according to claim 11, wherein said valve stem has a hollow center cavity opening towards said ventilation port, said hollow center cavity being in open communication with said patient connection port.

13. An assembly according to claim 12, wherein said stem includes a slot transverse said hollow center cavity, said slot being positioned in registration with said patient connection port when said stem is in either of said first or second positions.

14. An assembly according to claim 13, wherein said stem includes:
  a wall with an outer surface in sealing relationship with said access port when said stem is in said first position; and
  an opening through said wall into said hollow center cavity, said opening being positioned and configured to register with said access port when said stem is in said second position.

15. The interface assembly of claim 11 wherein the access port is structured and arranged to accommodate axial advancement and retraction of a catheter assembly while maintaining positive end expiratory pressure within the interior chamber, said catheter assembly comprising a suction catheter and a clip associated with the suction catheter, said suction catheter having a distal end portion for advancement through said access port and a proximal end, said clip being selectively located at a point defining the transition from said distal end portion and said proximal end, wherein the proximal end is to not be advanced beyond said access point.

16. An interface assembly for closed system endotracheal ventilating and aspirating procedures, comprising:
   a manifold having:
      a ventilation port in open communication with an interior chamber;
      a patient connection port in open communication with said interior chamber and forming a fluid flow path with said ventilation port, said patient connection port being substantially in registration with said ventilation port; and
      an access port in communication with said interior chamber and substantially out of registration with said patient connection port;
      said access port and patient connection port being positioned to provide a catheter travel pathway between said access port and said patient connection port, said catheter travel pathway including a portion of the fluid flow path from said interior chamber throughout said patient connection port; and
   a catheter assembly having:
      a suction catheter, including a proximal end, and a distal end portion for selective advancement and retraction through said access port;
      a flexible sheath carrying and substantially enveloping said suction catheter; and
      a clip positioned outside the flexible sheath and selectively attachable to the catheter through the sheath to selectively define the transition point between said proximal end and said distal end portion.

17. The interface assembly of claim 16, further including a valve, comprising:
   a stem positioned within said interior chamber constructed and arranged for movement between:
      a first position in which said stem blocks fluid flow through said access port; and
      a second position in which said stem provides a portion of said catheter travel pathway; and
   said valve being structured and arranged to allow movement of said stem between said first and second positions;
   said valve being further constructed and arranged to avoid blocking fluid flow between said ventilation port and said patient connection port.

18. An interface assembly for closed system neonatal endotracheal ventilating and aspirating procedures, comprising:
   a manifold, including a proximal manifold end and a distal manifold end, defining an interior chamber and having:
      a patient connection port at said distal manifold end in open communication with said interior chamber;
      a ventilation port at said proximal manifold end in open communication with said interior chamber, wherein a fluid flow path is formed through said interior chamber between said ventilation port and said patient connection port; and
      an access port at said proximal manifold end in open communication with said interior chamber, wherein a catheter travel pathway is provided through the access port, the interior chamber and the patient connection;
      said catheter travel pathway and fluid flow path being separated throughout said interior chamber between said proximal end and said distal end by a wall.

19. The interface assembly of claim 18, wherein an irrigation access tube is in fluid communication with said access port whereby respiratory therapy fluid may be introduced.

20. The interface assembly of claim 19, wherein said patient connection port is substantially in registration with said ventilation port and substantially out of registration with said access port.

* * * * *